United States Patent [19]

Klenk et al.

[11] 4,209,461
[45] * Jun. 24, 1980

[54] PROCESS FOR THE PRODUCTION OF BENZOYL CYANIDE (I)

[75] Inventors: Herbert Klenk, Hanau; Theodor Lüssling, Constance; Alfred Maierhofer, Allensbach; Heribert Offermanns, Hanau; Hans Wagner, Constance, all of Fed. Rep. of Germany

[73] Assignee: Deutsche Gold- und Silber-Scheideanstalt Vormals Roessler, Frankfurt, Fed. Rep. of Germany

[ * ] Notice: The portion of the term of this patent subsequent to Sep. 12, 1995, has been disclaimed.

[21] Appl. No.: 965,691

[22] Filed: Dec. 1, 1978

[30] Foreign Application Priority Data

Dec. 2, 1977 [DE] Fed. Rep. of Germany ....... 2753656

[51] Int. Cl.² ............................................. C07C 63/06
[52] U.S. Cl. ............................................... 260/545 R
[58] Field of Search ..................................... 260/545 R

[56] References Cited

U.S. PATENT DOCUMENTS 4,113,773  9/1978  Klenk et al. .......................... 260/545

FOREIGN PATENT DOCUMENTS 2611242  10/1977  Fed. Rep. of Germany ........... 260/565

OTHER PUBLICATIONS

Koenig, "Tetrahedron Letters", No. 26, pp. 2275–2278 (1974).
Organic Syntheses Collective, vol. 3, pp. 112–114.
Normant, Bull. Soc. Chim. (France), pp. 2402–2403 (1972).
Z. Phys. Chem., vol. 192 (1943), pp. 200–201.

*Primary Examiner*—Bernard Helfin
*Assistant Examiner*—L. Hendriksen
*Attorney, Agent, or Firm*—Cushman, Darby & Cushman

[57] ABSTRACT

The process described in Klenk U.S. Pat. No. 4,113,773 is improved by employing alkali metal cyanide in which at least half of the alkali metal cyanide has a particle size below 0.4 mm and the remainder has a particle size below 1.0 mm.

25 Claims, No Drawings

PROCESS FOR THE PRODUCTION OF BENZOYL CYANIDE (I)

BACKGROUND OF THE INVENTION

The present invention is directed to an improvement in the process disclosed and claimed in Klenk U.S. Pat. No. 4,113,773 (related to German application P 2,624,891). The entire disclosure of the Klenk patent is hereby incorporated by reference and relied upon.

It is known to produce benzoyl cyanide by the action of over stoichiometrical amounts of copper (I) cyanide on benzoyl chloride. The reaction is carried out at temperatures up to 80° C. in acetonitril or benzonitrile or in ether with the addition of over stoichiometrical amounts of lithium chloride or lithium iodide (Normant et al, Bull. Soc. Chim. France (1972) pages 2402–2403) or at temperatures of 220° to 230° C. in the absence of a solvent (Org. Synth. Coll. 3, 112–114). At best these processes give a yield of 65%.

It is also known to convert benzoyl chloride to benzoyl cyanide by means of an alkali cyanide in a two phase system consisting of water and a solvent which is immiscible with water in the presence of a quaternary alkyl ammonium salt (Tetrahedron Letters No. 26 (1974), pages 2275 to 2278). In this process the yield only amounts to 60%.

Furthermore, it is known to produce benzoyl cyanide from benzoyl chloride by reacting water free hydrogen cyanide and an at least equimolar amount of pyridine (Z. Phys. Chem. 192 (1943), 200–201). This process gives yields of 78%.

A disadvantage of the known process is that there are formed by-products to a considerable extent, particularly the dimer of benzoyl cyanide (the benzoyloxyphenyl malodinitrile). Consequently, not only the yield of benzoyl cyanide is unsatisfactory but also its purity. Benzoyl cyanide can be separated from its dimer only with considerable difficulty and even then only incompletely.

Finally, it is known to carry out the reaction of benzoyl chloride to benzoyl cyanide in the presence of catalytic amounts of heavy metal cyanides by means of stoichiometric amounts of alkali metal cyanide at temperatures of 100° to 300° C. (German OS 2,614,242). The disadvantage of this process is that the benzoyl chloride is not completely reacted and the benzoyl cyanide recovered is contaminated by benzoyl chloride.

In Klenk U.S. Pat. No. 4,113,773 it is stated that the reaction according to the invention is carried out at temperatures of about 50° to 160° C., preferably at temperatures of 90° to 130° C. Although the pressure can be selected essentially at random (i.e., it is not critical) in order to use a simple apparatus it is advantageous to use a pressure which does not vary substantially from normal pressure, e.g., to use atmospheric pressure. In many cases because of the presence of volatile substances it can be suitable to use an elevated pressure corresponding to the temperature.

In several cases, it can be advantageous to add an inert solvent as a diluent. As such, inert solvents there can be used for example hydrocarbons, e.g., aromatic hydrocarbons such as benzene, toluene or xylene as well as mesitylene, ethyl benzene, cumene, p-cymene, t-butyl benzene or 1,3,5-triethyl benzene or aliphatic hydrocarbons such as ligroin with a boiling range of about 90° to 140° C., octane or decane or cyclic hydrocarbons such as decalin, cyclohexane and tetralin or halogenated hydrocarbons, particularly chlorinated aromatic or aliphatic hydrocarbons such as chlorobenzene, symmetrical tetrachloroethane, carbon tetrachloride, trichloroethylene, trimethylene bromide, ethylene dibromide. Also as the solvent there can be used for example ethers, e.g., dioxane, dibutyl ether, dioxolane, ethylene glycol diethyl ether, ethylene glycol dibutyl ether, ethylene glycol dimethyl ether or esters, e.g., alkyl esters such as butyl acetate, propyl acetate, amyl acetate, isobutyl acetate, octyl acetate, ethyl propionate, methyl butyrate, ethyl butyrate or methyl valerate. When an inert solvent is employed, the amount is not critical but it can be used for example in an amount of 10 to 5000 ml per mole of benzoyl chloride.

According to the invention the reaction takes place with alkali cyanides. Preferably there is used sodium cyanide or potassium cyanide. There also can be used lithium cyanide. Generally, it is suitable to employ at least a stoichiometric amount of cyanide. Advantageously, there is used about 1.05 to 3.0 equivalents of cyanide, especially 1.05 to 1.5 equivalents of cyanide, per mole of benzoyl chloride.

The reaction takes place in the presence of carboxylic acid nitriles. There can be used nitriles which are liquid under the reaction conditions and which are not changed. Especially suited are saturated aliphatic monocarboxylic acid nitriles of saturated aliphatic monocarboxylic acids with 2 to 6 carbon atoms, e.g., alkyl nitriles especially acetonitrile and isobutyronitrile. Other suitable nitriles include propionitrile, butyronitrile, valeronitrile, capronitrile or lauronitrile or unsubstituted aryl nitriles such as benzonitrile, o-toluo-nitrile, p-toluonitrile or m-toluonitrile.

The reaction furthermore takes place in the presence of copper (I) salts. There can be used both simple and complex copper (I) salts, particularly for example copper (I) cyanide, copper (I) chloride, copper (I) bromide and potassium tetracyanocuprate (I). There can also be used copper (I) fluoride, copper (I) iodide, copper (I) sulfate, copper (I) thiocyanate and sodium tetracyanocuprate (I).

The amount of nitrile and copper (I) salt to use depends in a given case on the type of nitrile and copper (I) salt and the reaction conditions, such as temperature and pressure, and in a given case on the type and amount of the solvent used as a diluent.

Generally, it is suitable to add at least 0.05 mole of nitrile per mole of benzoyl chloride. Although the nitrile can be used in a many times molar excess, it is advantageous to use not more than about 2 moles of nitrile per mole of benzoyl chloride. Preferably there is employed 0.1 to 1.0 mole of nitrile, especially 0.1 to 0.5 mole of nitrile.

It is generally suitable to use about 0.05 to 1.0 equivalent of copper (I) salt per mole of benzoyl chloride. Preferably there is employed 0.05 to 0.5 equivalent of copper (I) salt per mole of benzoyl chloride.

The cyanide is added as alkali cyanide. If the copper (I) salt used is a cyanide there can be eliminated entirely or partially an equivalent amount of alkali cyanide. However, it is generally advantageous to include not more than about 0.5 equivalent of cyanide in the form of copper salts.

SUMMARY OF THE INVENTION

It has now been found that the process for the production of benzoyl cyanide by reaction of benzoyl chloride with metal cyanides at elevated temperature according to Klenk U.S. Pat. No. 4,113,773 (and German P 2624891)can be carried out in a particularly advantageous manner if at least half of the alkali metal cyanide, e.g., sodium cyanide or potassium cyanide, has a particle size below 0.4 mm and the rest has a particle size below 1.0 mm. This method of operation is outstandingly suited for use of the process on an industrial scale. The benzoyl cyanide is recovered in excellent purity and is especially as good as free from dimers.

The reaction of the benzoyl chloride with the alkali metal cyanide takes place in the presence of the carboxylic acid nitrile and copper (I) salts and in a given case, in the presence of inert solvents. Thus there can be used the nitriles, copper (I) salts and inert solvents mentioned above in connection with the Klenk patent.

As alkali metal cyanide there can be employed a commercial article which, if necessary, is comminuted to the stated particle size. It is particularly favorable if the alkali metal cyanide has at least 80% with a particle size below 0.4 mm.

The alkali metal cyanide used is preferably potassium cyanide or even more preferably sodium cyanide. *)
Unless otherwise indicated all parts and percentages are by weight.
*) Preferably there are employed 1.05 to 1.50 and especially 1.05 to 1.20 equivalents of cyanide per mole of benzoyl chloride.

The process can comprise, consist essentially of or consist of the steps set forth and the materials can comprise, consist essentially of or consist of those set forth.

EXAMPLE I

There were present in a reaction vessel provided with a reflux condenser a mixture of 141 grams (1.0 mole) of benzoyl chloride and 25 ml of acetonitrile and the mixture was heated to 112° C. Then there were added in the course of 60 minutes a suspension of 9 grams of copper (I) cyanide (0.1 mole) and 44 grams of sodium cyanide (1.1 mole) in 79 ml of xylene. The sodium cyanide had 13% with a particle size below 0.1 mm, 41% with a particle size between 0.1 and 0.2 mm, 23% with a particle size between 0.2 and 0.4 mm and 23% with a particle size between 0.4 and 0.8 mm. The temperature of the mixture increased slowly to 128° C. during the addition of the suspension. Then the mixture was held at this temperature for a further 90 minutes and subsequently cooled to 18° C. The salt, chiefly sodium chloride, which separated was filtered off and washed with 25 ml xylene. The filtrate was distilled under reduced pressure. There were obtained 121 grams of pure benzoyl cyanide, corresponding to a yield of 93% based on the benzoyl chloride added. The benzoyl cyanide contained no benzoyl chloride. It had a boiling point of 115° to 117° C. at 45 mbar.

EXAMPLE II

The procedure was the same as in Example I except there was added a sodium cyanide which had 53% of a particle size below 0.1 mm, 42% of a particle size between 0.1 and 0.2 mm and 5% of a particle size between 0.2 and 0.8 mm. The yield of benzoyl cyanide was 122 grams corresponding to 93% based on the benzoyl chloride added. The benzoyl cyanide was free of benzoyl chloride. It had a boiling point of 113° to 116° C. at 41 mbar.

What is claimed is:

1. In a process for preparing benzoyl cyanide by reacting an alkali metal cyanide with benzoyl chloride in the presence of a copper (I) salt at a temperature of about 50° to 160° C. in the presence of a carboxylic acid nitrile inert under the reaction conditions the improvement comprising employing alkali metal cyanide having a particle size range in which at least half of the alkali metal cyanide has a particle size below 0.4 mm and the remainder has a particle size below 1.0 mm.

2. A process according to claim 1 wherein the copper (I) salt is copper (I) cyanide, copper (I) chloride, copper (I) bromide or potassium tetracyanocuprate (I).

3. A process according to claim 2 wherein the alkali cyanide is sodium cyanide or potassium cyanide.

4. A process according to claim 2 wherein there is used 0.1 to 3.0 equivalents of cyanide per mole of benzoyl chloride.

5. A process according to claim 4 wherein there is used 1.05 to 1.5 equivalents of cyanide per mole of benzoyl chloride.

6. A process according to claim 5 wherein there is used 0.1 to 0.5 mole of carboxylic acid nitrile per mole of benzoyl chloride.

7. A process according to claim 6 wherein there is used 0.05 to 0.5 equivalents of copper (I) salt per mole of benzoyl chloride.

8. A process according to claim 2 wherein there is used 0.05 to 2 moles of carboxylic acid nitrile per mole of benzoyl chloride.

9. A process according to claim 8 wherein the nitrile is a liquid alkyl nitrile.

10. A process according to claim 9 wherein the nitrile has 2 to 6 carbon atoms.

11. A process according to claim 10 wherein the nitrile is acetonitrile or isobutyronitrile.

12. A process according to claim 8 wherein there is used 0.01 to 0.5 mole of carboxylic acid nitrile.

13. A process according to claim 2 wherein there is used 0.05 to 1.0 equivalent of copper (I) salt per mole of benzoyl chloride.

14. A process according to claim 13 wherein there is used 0.05 to 0.5 equivalent of copper (I) salt mole of benzoyl chloride.

15. A process according to claim 2 wherein the temperature is 90° to 130° C.

16. A process according to claim 2 carried out in the presence of an inert organic solvent as a diluent.

17. A process according to claim 16 wherein the inert solvent is a hydrocarbon or halohydrocarbon.

18. A process according to claim 2 wherein the inert solvent is an aromatic hydrocarbon, an aliphatic hydrocarbon, a chlorinated aromatic hydrocarbon or a chlorinated aliphatic hydrocarbon.

19. A process according to claim 18 wherein the inert solvent is benzene, toluene, xylene, ligroin boiling at about 90° to 140° C., chlorobenzene, dichlorobenzene or tetrachloroethane.

20. A process according to claim 2 wherein the copper (I) salt is copper (I) chloride, copper (I) bromide or potassium tetracyanocuprate (I).

21. A process according to claim 2 wherein the copper (I) salt is copper (I) cyanide.

22. A process according to claim 1 wherein the copper (I) salt is copper (I) cyanide, copper (I) chloride, copper (I) bromide, potassium tetracyanocuprate (I), copper (I) fluoride, copper (I) iodide, copper (I) sulfate, copper (I) thiocyanate or sodium tetracyanocuprate (I).

23. A process according to claim 1 wherein the alkali metal cyanide has at least 80% with a particle size below 0.4 mm.

24. A process according to claim 23 wherein there is used 1.05 to 1.20 equivalents of cyanide per mole of benzoyl chloride.

25. A process according to claim 1 wherein there is used 1.05 to 1.20 equivalents of cyanide per mole of benzoyl chloride.

* * * * *